United States Patent [19]

Doyle et al.

[11] Patent Number: 4,852,955

[45] Date of Patent: Aug. 1, 1989

[54] MICROSCOPE FOR USE IN MODULAR FTIR SPECTROMETER SYSTEM

[75] Inventors: Walter M. Doyle, Laguna Beach; Norman S. Hughes, San Clemente, both of Calif.

[73] Assignee: Laser Precision Corporation, Irvine, Calif.

[21] Appl. No.: 907,993

[22] Filed: Sep. 16, 1986

[51] Int. Cl.$^4$ .................... G02B 5/10; G02B 13/14; G02B 21/18

[52] U.S. Cl. .................... 350/1.2; 350/511; 350/620

[58] Field of Search .............. 350/1.2, 505, 511, 526, 350/620

[56] References Cited

U.S. PATENT DOCUMENTS

| | | | |
|---|---|---|---|
| 3,134,297 | 5/1964 | Carlson et al. | 350/1.2 X |
| 3,464,757 | 9/1969 | Schmidt et al. | 350/1.2 |
| 4,594,509 | 6/1986 | Simon et al. | 250/353 X |
| 4,712,912 | 12/1987 | Messerschmitt | 356/73 |

OTHER PUBLICATIONS

BioRad Digilab publication, date unknown.
ESN–European Spectroscopy News, 64(1986), p. 12. XS
"Low-Cost FTIR Microscopy Units Gain Wider Use in Microanalysis", C&EN, Dec. 9, 1985, p. 15.
Analect Instruments Publication, Jan., 1986.

Primary Examiner—Bruce Y. Arnold
Assistant Examiner—David J. Edmondson
Attorney, Agent, or Firm—Thomas J. Plante

[57] ABSTRACT

A microscopic unit for a multi-station modular FTIR spectrometer system is disclosed. The microscope unit, which has a Cassegrain objective, not only provides the usual optical path for radiation during visual observation, and for infrared radiation in the transmission mode, but also provides a separate optical path for infrared radiation in the reflectance mode and in a macroscopic transmission mode. An optical switching wheel is in the path of entering radiation, which may enter through any of three ports; and the wheel is movable into a plurality of alternative positions, including a position in which radiation entering through one port passes through the wheel toward the objective, a position in which radiation entering through the same port is reflected by a wheel-carried mirror along the separate optical path, a position in which a wheel-carried mirror causes radiation to bypass the microscope, and positions in which other wheel-carried mirrors reflect into the microscope radiation entering through other ports.

14 Claims, 7 Drawing Sheets

MICROSCOPE FOR USE IN MODULAR FTIR SPECTROMETER SYSTEM

BACKGROUND OF THE INVENTION

This invention relates to microscopes used in Fourier Transform infrared (FTIR) spectrometer systems. The disclosed microscope is intended to be part of a modular system, in which the function of microscopic analysis is only one of several (or many) options readily available to the operator.

Industrial and forensic chemists have been turning increasingly to infrared microscopy as a problem-solving adjunct to Fourier-transform infrared (FTIR) spectroscopy. The combined technique uses a microscope attachment to an FTIR spectrophotometer to get transmission or reflectance spectra of regions or particles less than 10 micrometers in diameter. One reason for the rising popularity of the method is that detailed chemical information can be obtained from very small samples or highly localized regions. Another reason is the recent availability of low-cost, benchtop FTIR spectrophotometers with optics good enough for the purpose.

Microscopes of this type in themselves have multiple uses. They permit microscopic observation in the visual range, and also permit infrared analysis of the sample, using the modulated output beam of an interferometer spectrometer. The visual mode is also used to move the sample into place for use of the IR analytical beam. Additionally, the IR beam may be designed to analyze the sample in either the transmission mode or the reflectance mode.

Providing an effective reflectance mode has been a major challenge for the suppliers of FTIR microscopes, because of the very low radiation throughput obtained in the reflectance mode of most FTIR microscopes. This problem is effectively dealt with in a copending application assigned to the assignee of the present application application Ser. No. 907,995, filed Sept. 16, 1986.

In general, FTIR microscopes have not been designed in such a way as to fit into a versatile FTIR spectrometer system. In fact, truly versatile systems of this type have only recently been developed, as disclosed in two other copending, common assignee applications application Ser. No. 895,211, filed Aug. 11, 1986; and application Ser. No. 900,730, filed Aug. 27, 1986. Those applications relate, respectively, to ensuring maximum radiation throughput in a multi-unit spectrometer system, and to providing modular "building blocks" which permit cost-effective and functionally efficient assembling and re-assembling of such multi-unit spectrometer systems.

SUMMARY OF THE INVENTION

The present invention incorporates in an FTIR microscope unit an optical switching apparatus, in the form of a wheel carrying a plurality of reflecting mirrors, and having at least one position in which entering radiation is not interrupted. The wheel is movable by the operator to any one of its operative positions, depending on the experiment which will be conducted.

The present invention also provides the option of having two separate focusing radiation beams within the microscope housing. The first beam is the usual radiation which passes through the objective lens. The second beam can be used either for sample analysis independently of the microscope, or for directing a beam through the objective lens when the microscope is used in the reflectance mode. Because the second beam travels between two confocal, reflecting mirrors, it provides the radiation throughput advantage disclosed in U.S. Ser. No. 895,211.

Another feature of the present invention is the ability of the optical switching device to cause the entering IR beam from the interferometer to bypass the microscope. Thus the IR beam can be used in another accessory in the spectrometer system, without requiring removal of the microscope unit from the system.

DETAILED DESCRIPTION OF PREFERRED EMBODIMENT

Figure 1:
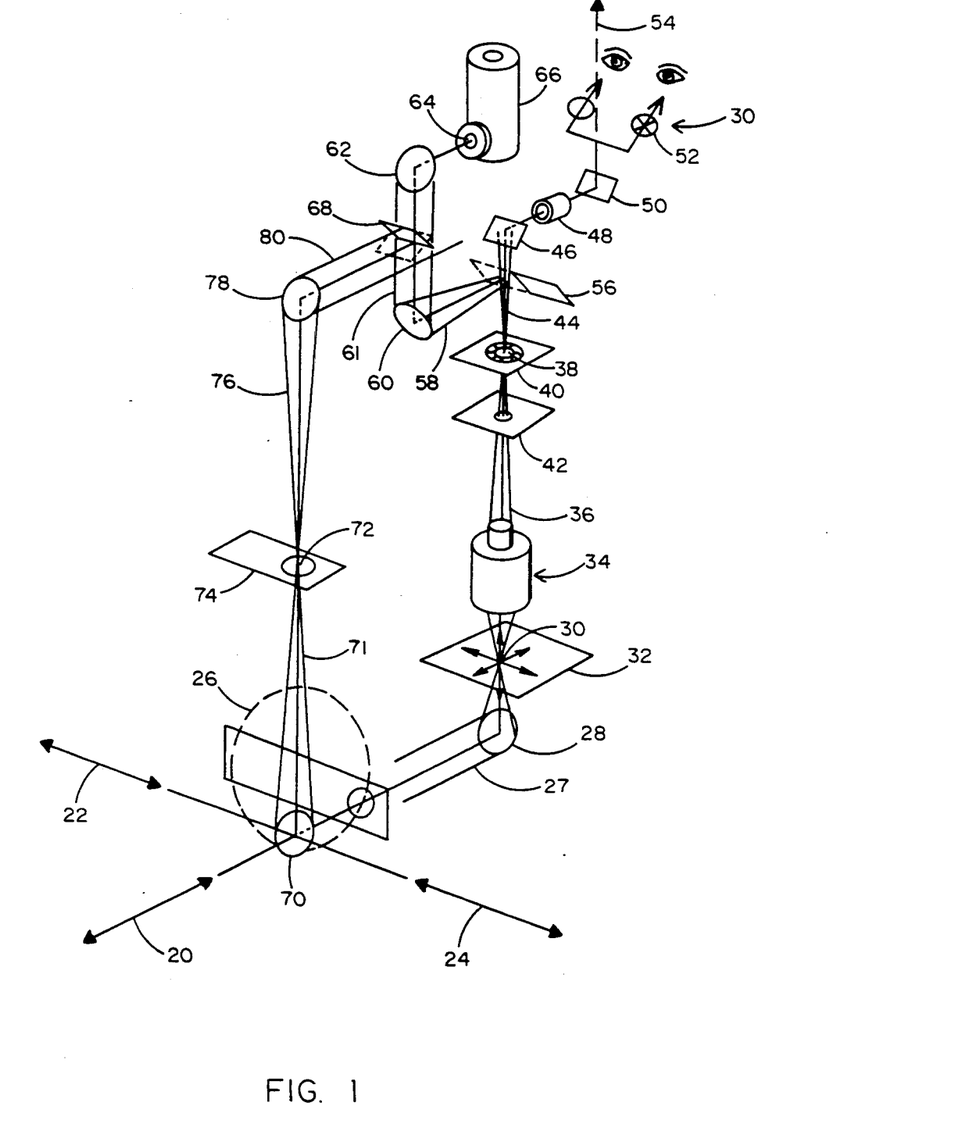
FIG. 1 is a diagrammatic showing of the microscope optical system.

The diagrammatic sketch of FIG. 1 provides a complete summary of the optical system included in the microscope assembly of the present invention. One of the advantages of this microscope assembly is that it includes optical elements which are not intrinsic parts of the microscope function, but which permit the microscope assembly to function as part of a flexible, multi-accessory spectrometer system of the type disclosed in U.S. Ser. No. 895,211 and U.S. Ser. No. 900,730.

Three beam entry-exit directions are provided, symbolized by lines 20, 22, and 24, each of which has bidirectional arrows indicating that radiation may go into or out of the microscope in any of these three directions. The direction represented by line 20 is rearward from the microscope housing; the direction represented by line 22 is rightward from the microscope housing (as viewed from the front, or eyepiece, side); and the direction represented by line 24 is leftward from the microscope housing (as viewed from the front side). Generally, radiation entering along line 20 will be a collimated beam output by the interferometer (not shown).

After the entering beam, from any of the three directions, passes through its aperture into the microscope chamber, it will reach the position of a mirror-carrying wheel, indicated by dashed line 26. This wheel is an optical switching device which may be rotated to, and locked in position at, any one of six available positions. In at least one position, the wheel simply provides an aperture through which a collimated beam 27 entering on line 20 will pass directly to a parabolic mirror 28, which is used when the microscope is in the transmission mode. For viewing through an eyepiece 30, the incoming collimated radiation will be a collimated white light, or visible, beam. For infrared analysis, the incoming radiation will be a collimated IR beam.

Parabolic mirror 28, which has a short focal length, causes the reflected beam 29 to focus at point 30, which is the sample location. The sample is supported on a platform 32, which is position-adjustable under operator control in X, Y and Z axes, in order to bring the sample into the focal point.

After passing through the focal point, the diverging rays of radiation beam 33 enter a Cassegrain objective 34, which contains reflective surfaces for microscopic viewing of the sample. The focusing beam 36 leaving lens 34 reaches its focal point at 38, which is in the plane of a stop, or iris, 40, the size of which is adjustable under operator control. A filter/polarizer holder 42 is located between lens 34 and stop 40.

After focusing at 38, a diverging beam 44 is reflected by a flat mirror 46 into an image transfer lens 48, from which the exiting beam is directed by another flat mirror 50 to eyepiece 30 for binocular viewing, and also for position adjustment using a cross hair guide 52 located in one of the tubes of the eyepiece. As shown by dashed line 54, the light may be directed toward a TV camera.

Note that a flat, movable view/test mirror 56 is in its solid line position during visual inspection and position-location of the sample. Mirror 56 is moved to its dashed line position when infrared radiation is being transmitted through the microscope. In the infrared transmission mode, IR radiation from the interferometer, entering along path 20, follows the same path as that described for the visible radiation, until it is reflected by mirror 56 to provide diverging beam 58.

Beam 58 is recollimated by a parabolic mirror 60, and directed as beam 61 toward another parabolic mirror 62, which causes the radiation to focus at a detector 64, enclosed in a Dewar cooling unit 66. Note that a movable mirror 68, in this mode, must be in a position in which it does not block the collimated beam 61. Mirror 68 has a total of three available positions, two of which are reflecting positions, as will be explained below.

In one or more positions of mirror-carrying wheel 26, the entering collimated radiation will be reflected by a parabolic mirror 70 on the wheel to provide focusing radiation 71 directed toward focal point 72. In one mode of operation, transmission illumination of a sample will be made if a sample has been placed on a sample slide 74. This will provide macroscopic sample illumination, as distinguished from microscopic sample illumination by the Cassegrain 34. After focusing at 72, a diverging radiation beam 76 will be reflected and recollimated by a parabolic mirror 78.

The radiation path between confocal paraboloids 70 and 78 is a radiation path separate from that of radiation passing through lens 34. This separate path provides a plurality of advantages for the microscope accessory unit. First, as previously stated, it permits non-microscopic sample illumination at 72. Second, when no sample is present at 72, the confocal paraboloids 70 and 78 provide a throughput-conserving segment of the radiation path, as disclosed in U.S. application Ser. No. 895,211. Third, this separate path permits high radiation throughput in the reflectance mode, as disclosed in U.S. application Ser. No. 907,995.

In the reflectance mode, no sample is present at focal point 72. Collimated beam 80, reflected by mirror 78, will be partially reflected by movable mirror 68. This is a 100% reflective mirror, which has been moved to a position in which it reflects half of beam 80 toward the Cassegrain 34 and the sample at 30. This 50% beam is caused by parabolic mirror 60 to focus at point 38, having been reflected toward that point by flat mirror 56, which has been moved into its dashed line position. This radiation will, as explained in detail in U.S. Ser. No. 907,995, pass downwardly through Cassegrain objective 34, be reflected by the sample at 30, pass upwardly through objective 34, and pass through focal point 38. It will then be reflected by flat mirror 56, and be recollimated by parabolic mirror 60 in the form of a 50% beam which bypasses mirror 68, and reaches detector 64.

In one or more positions of mirror-carrying wheel 26, the incoming radiation will be reflected perpendicularly, so as to bypass the microscope unit, and travel to another accessory. This reflection may be accomplished by a parabolic mirror which also provides a collimated beam/focused beam conversion, thereby obtaining the throughput-conservation benefits disclosed in U.S. Ser. No. 895,211.

Figure 2:
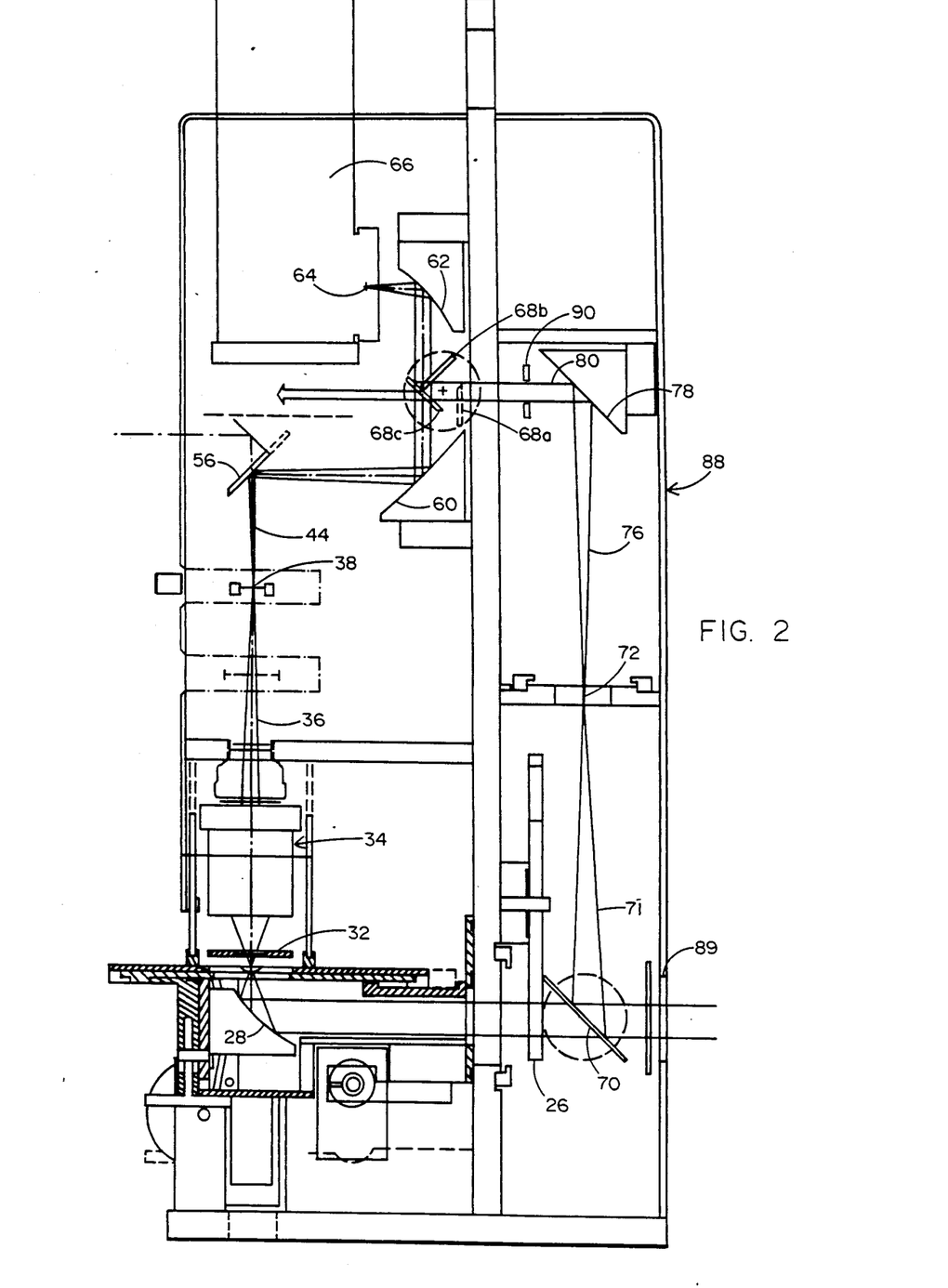
FIG. 2 is a side view of the microscope showing the primary microscope components.
Figure 3:
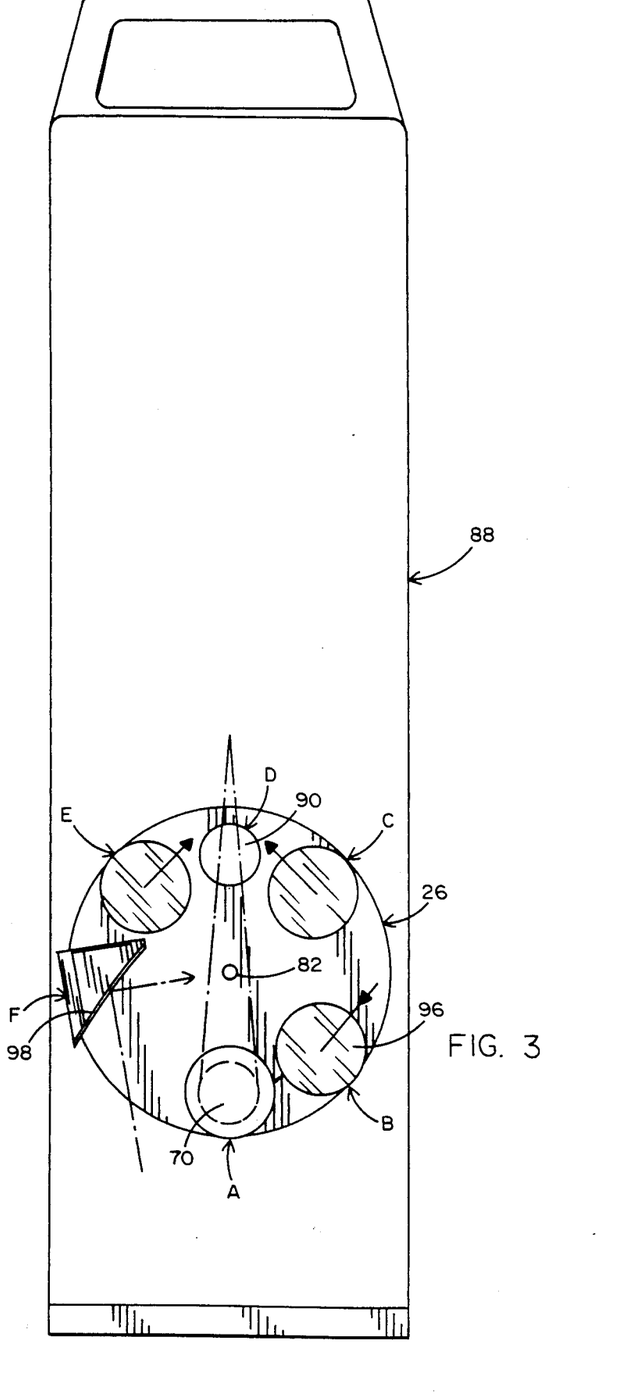
FIG. 3 is a rear view of the microscope of FIG. 2, which shows the mirror-carrying face of the optical switching wheel.
Figure 4:
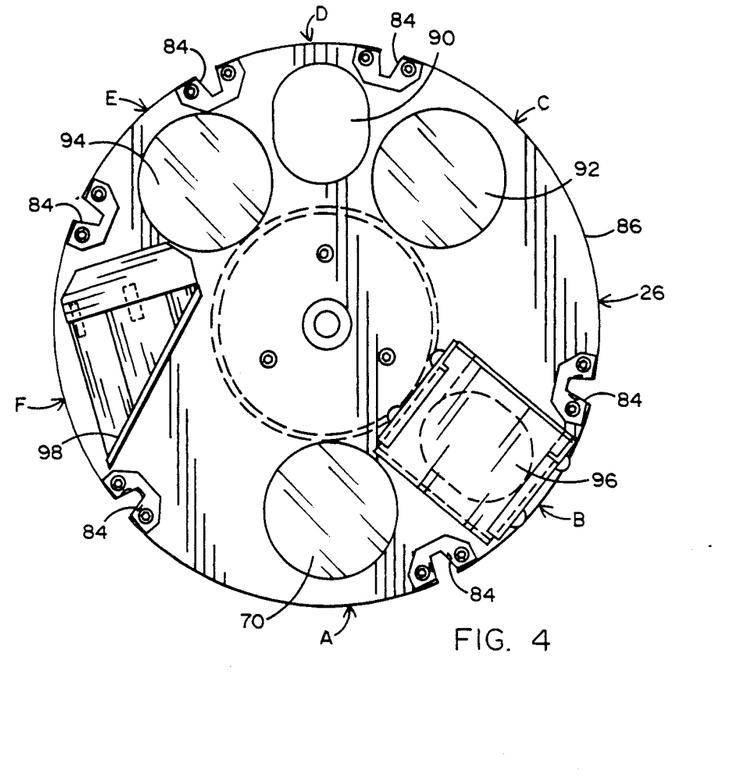
FIG. 4 is a view showing, in greater detail, the structure of the optical switching wheel, also looking at the mirror-carrying face of the wheel.
Figure 5:
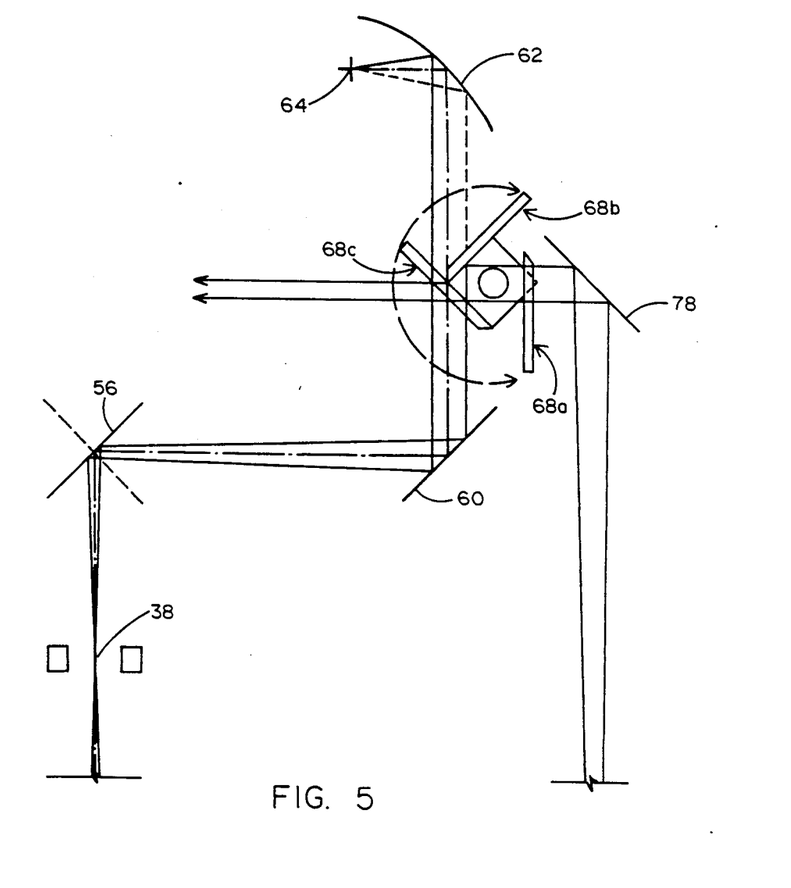
FIG. 5 is a close-up of the optical switch component which is used to divide the incoming beam in the reflectance mode.

FIGS. 2 and 3 are side and rear elevation views, respectively, of the internal elements of the microscope unit, which are enclosed in a housing 88. FIG. 4 is a more detailed view of the mirror-carrying wheel 26. FIG. 5 is a closeup of the three-position mirror 68. Except where new numerals are designated, the numerals used in FIG. 1 are used in the other figures to identify corresponding parts and locations.

As seen in both FIG. 3 and FIG. 4, wheel 26 is movable around an axis 82. The number of available positions of wheel 26 is dictated in part by the desired dimensions of the microscope accessory unit. In the illustrated version, six positions are provided. The incoming radiation is controlled by whichever part of the wheel is located at the bottom in the selected position. After rotation by the operator to its desired position, wheel 26 is locked in that position by engaging a pin (not shown) in one of the six notches 84 (FIG. 4) provided in the periphery 86 of the wheel. Preferably, the locking pins are spring-biased toward the locking position, and are temporarily held out of the notches by a manually controlled lever.

The six operative positions are indicated by the letters A-F. In position A, which is shown in line with the incoming radiation in FIG. 2, long focal length parabolic mirror 70 reflects a collimated beam entering through rear port 89 (FIG. 2) to direct focusing beam 71 toward focal point 72. The diverging beam 76 above focal point 72 is recollimated by long focal length parabolic mirror 78, forming collimated beam 80. Note that a stop 90 may be used to block excessive radiation reflected by mirror 78, i.e., radiation which will not provide useful throughput in the remaining optical elements of the microscope unit.

In position D, an aperture 90 in the wheel allows collimated radiation (infrared or white light) entering through port 89 to pass directly to short focal length mirror 28, which reflects the radiation toward the Cassegrain 34. Or, if desired, a sample may be illuminated by the collimated beam before the radiation reaches mirror 28.

In positions C and E, a collimated beam (infrared or white light) entering rear port 89 is converted by a parabolic mirror 92 or 94 into a focused beam leaving through one of the side ports. As seen from the front of the microscope, the focused beam exits from the left side port when the wheel is in position C, and from the right side port when the wheel is in position E. In either case, the radiation bypasses the microscope accessory unit.

In position B, a 45° flat mirror 96 causes a collimated beam (infrared or white light) entering through a side port to be reflected to parabolic mirror 28, and thence toward Cassegrain 34.

In position F, a parabolic mirror 98 reflects a collimated beam (infrared or white light) entering one of the side ports, converting it into focusing beam 71 which passes through focal point 72.

In some instances, it will be useful to omit the mirror 92 of position C, in order to permit radiation to pass into one side port and out the other side port, in a direction parallel to the plane of the wheel.

In FIGS. 2 and 5, the three positions of mirror 68 are shown. When the microscope is used in the transmission mode, mirror 68 is in position 68a, out of the path of the radiation. When the microscope is used in the reflectance mode, mirror 68 is in position 68b, in which it reflects half of the collimated beam 80 toward the Cassegrain and sample. In its third position, 68c, the mirror reflects the entire collimated beam 80 toward detector 64. This occurs when the illuminated sample is at 72.

The remaining figures show the radiation paths caused by various positions of wheel 26, and mirror 68; and thus demonstrate the versatility of the microscope accessory unit.

Figure 6:
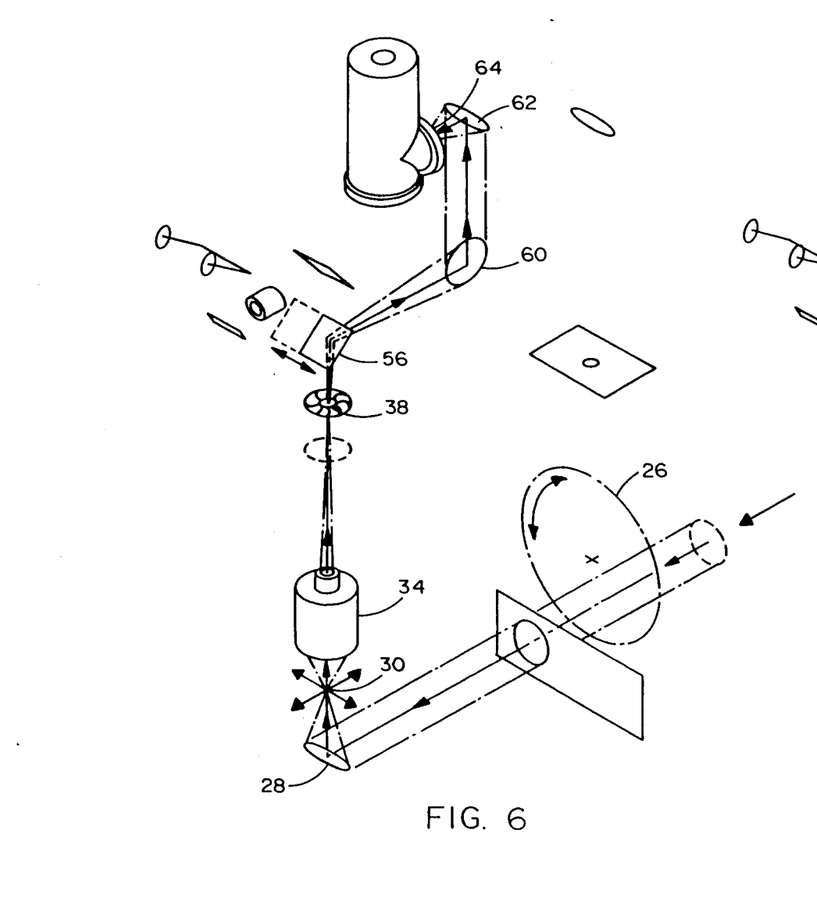
FIGS. 6–9 show the radiation paths in a variety of different operational modes of the mirrors in the microscope unit.

FIG. 6 shows the unit in its FTIR microscopic transmission mode. The collimated beam from the interferometer passes through the opening in wheel 26, and is reflected toward a sample at focal point 30 by short focal length paraboloid 28. The diverging beam leaving focal point 30 enters the Cassegrain objective 34. Leaving the Cassegrain, the radiation path is through adjustable stop 38, and is reflected by mirror 56 toward paraboloid 60. There the radiation is recollimated, and directed toward paraboloid 62, which focuses the radiation at detector 64.

Figure 7:
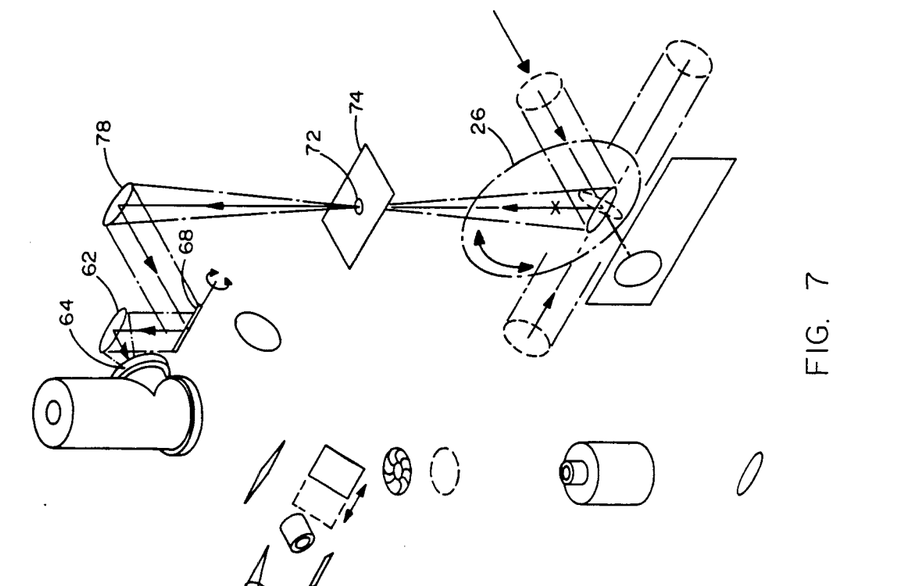

FIG. 7 shows the unit in its FTIR macroscopic transmission mode. The collimated entering beam is reflected by a long focal length paraboloid on wheel 26, providing focusing radiation traveling toward focal point 72, where it illuminates a sample carried by slide 74. The diverging beam leaving point 72 is recollimated by another long focal length paraboloid 78. This entire collimated beam is reflected upwardly by flat mirror 68, and is focused by paraboloid 62 at detector 64.

Figure 8:
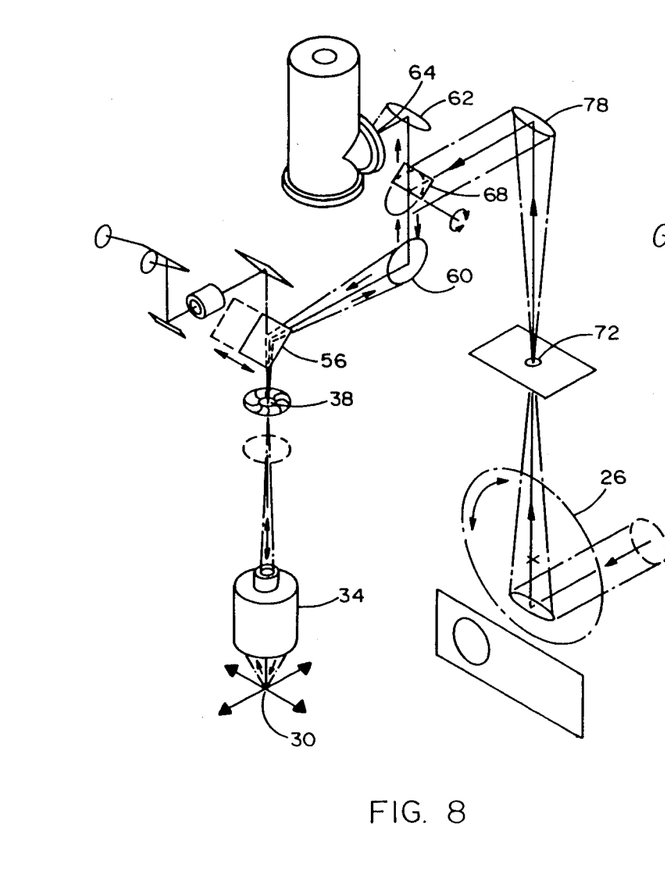

FIG. 8 shows the unit in its FTIR reflectance mode. The collimated entering beam is reflected by a paraboloid on wheel 26 upwardly toward focal point 72 (no sample being present at that point). The diverging beam leaving focal point 72 is recollimated by paraboloid 78, and directed toward flat mirror 68. In this case mirror 68 is in the position in which it reflects half of the collimated beam downwardly toward paraboloid 60. (The other half of the collimated beam from paraboloid 78 continues to the left, moving out of the optical system). As shown by the arrows, the reflected half of the collimated beam is focused by paraboloid 60 at adjustable stop 38, after being reflected downwardly by flat mirror 56. The diverging beam traveling downwardly from stop 38 enters Cassegrain 34, and is focused on, and reflected by, a sample at 30. The reflected radiation again passes through Cassegrain 34 and focal point 38. The diverging radiation traveling upwardly from point 38 follows the path shown by the arrows, to be recollimated by paraboloid 60, and then to travel upwardly, bypassing the edge of flat mirror 68. Thus this sample-reflected radiation reaches paraboloid 62 and detector 64.

Figure 9:
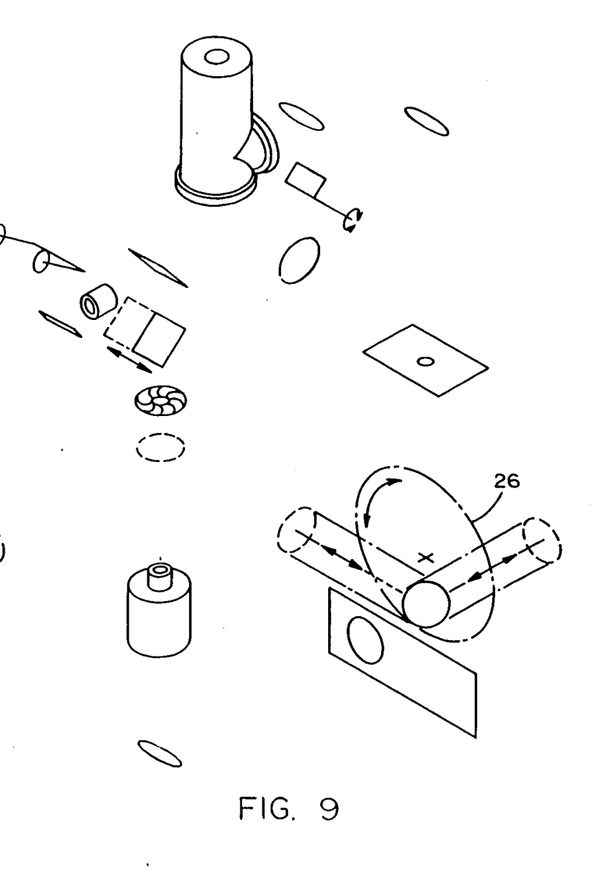

FIG. 9 shows the unit in the situation in which it is bypassed by the radiation in the spectrometer system. As shown by the arrows, radiation entering either of two ports in the housing may be caused by a mirror on the wheel 26 to exit by the other port. Both entering and exiting beams may be collimated, if a flat mirror is used. However, it is more likely that a paraboloid will be used, thus converting the beam from collimated to focusing, or vice versa. This conversion permits the system to benefit from the throughput-conserving techniques disclosed in U.S. Ser. No. 895,211.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. In an FTIR spectrometry apparatus having a source of infrared radiation, a source of visible radiation, and an interferometer which outputs an infrared beam; a microscope accessory unit operable in infrared transmittance and reflectance modes, comprising:
    a housing having one or more ports for entering radiation;
    a sample-supporting platform;
    a Cassegrain objective having a focus at the platform-supported sample;
    means for visually observing such sample;
    a detector for receiving infrared radiation from the sample through the objective;
    first optical means providing a first infrared radiation path along which the entering infrared radiation beam both travels through the Cassegrain and illuminates the sample in the transmittance mode, directional changes of the infrared radiation beam as it travels along said first path being caused solely by fully-reflecting mirrors;
    second optical means providing a second infrared radiation path along which the entering infrared radiation beam both travels through the Cassegrain and illuminates the sample in the reflectance mode, directional changes of the infrared radiation beam as it travels along said second path being caused solely by fully-reflecting mirrors and by the sample;
    the first and second infrared radiation paths first entering the Cassegrain from opposite directions, and the second radiation path traveling completely through the Cassegrain in both directions as it moves toward and away from the sample; and
    optical switching means for determining whether the entering infrared radiation travels along the first radiation path or along the second radiation path.

2. The apparatus of claim 1 in which the optical switching means is a wheel rotatable around its axis in such a way as to place a plurality of different segments of the wheel into a given position located in the path of the radiation entering the housing;
    one of those segments providing an aperture through the wheel through which radiation travels along one of the paths; and
    one of those segments carrying a first parabolic mirror which causes radiation to travel along the other path.

3. The apparatus of claim 2 which also comprises:
a second parabolic mirror, which is confocal with, and in the same radiation path as, the first parabolic mirror.

4. The apparatus of claim 2 wherein the wheel also carries another parabolic mirror which causes radiation entering one of the ports in the housing to exit through another port in the housing without reaching any other optical elements inside the housing.

5. The apparatus of claim 1 in which the second radiation path comprises:
a collimated radiation portion; and
a flat mirror which deflects approximately half of such collimated radiation into the objective in such a way that the radiation is reflected by a sample on the sample-supporting platform, and returns through the objective to the detector.

6. The apparatus of 5 which also comprises:
means for moving the flat mirror into three different positions, in the first of which it deflects partial radiation toward the objective, in the second of which it deflects the full radiation toward the detector, and in the third of which it is bypassed by radiation traveling through the objective.

7. The apparatus of claim 6 in which the mirror-moving means comprises a rotatable mirror-supporting member which carries the flat mirror in an eccentric position with respect to the axis of rotation of the supporting member, so that rotation of the mirror-supporting member changes both the location of the mirror and its angular position.

8. The apparatus of claim 5 in which:
the second radiation path has an initial portion extending substantially parallel to the portion which passes through the Cassegrain; and
the second radiation path also has a laterally-extending portion which joins the parallel portions of the path, and which includes the partially reflected collimated portion.

9. The structure of claim 1 which also comprises:
a second sample-supporting platform located in the second radiation path between the entering infrared radiation and the first sample-supporting platform.

10. The apparatus of claim 1 in which:
the first optical means, which provides the first optical path, receives entering collimated radiation and focuses it at the sample; and
the second optical means, which provides the second optical path, receives entering collimated radiation, directs the radiation initially along a path laterally spaced from the first path, then toward the location of the first path, and then toward the sample on a path co-linear with, but in opposite direction to, the first path.

11. The apparatus of claim 10 in which:
the initial portion of the second path includes two confocal parabolic mirrors, one of which receives the entering collimated radiation and reflects it as converging radiation toward a focal point, and the other of which receives diverging radiation from the focal point and reflects it as a collimated beam toward the location of the first path.

12. For use with a spectrometer having an infrared radiation source and an infrared radiation detector, a microscope unit, which receives the radiation beam from the source and causes it to illuminate a sample, comprising:
an objective which focuses the radiation beam either before or after that radiation has illuminated the sample;
means for directing the radiation beam along a first path which provides transmission illumination of the sample by causing the radiation to pass through the sample, then to pass through the objective, and then to pass to the detector;
means for directing the radiation beam along a second path which provides reflectance illumination of the sample by causing the radiation to pass through the objective in one direction toward the sample, to pass through the objective in the opposite direction after reflectance at the sample, and then to pass to the detector;
one of the radiation paths including two confocal parabolic reflectors between which the radiation beam travels prior to its reaching the objective; and
optical switching means whose position determines whether the radiation beam will be directed along the first path or the second path.

13. The structure of claim 12 in which the second radiation path contains the two confocal parabolic reflectors and the portion of the path between such confocal reflectors is substantially parallel to the radiation path through the objective.

14. The structure of claim 12 in which the optical switching means is a rotatable member having a plurality of positions for controlling the radiation beam from the source, in one of which positions the beam from the source is reflected by one of the confocal parabolic reflectors.

* * * * *